US008835396B2

(12) United States Patent
Verlaan et al.

(10) Patent No.: US 8,835,396 B2
(45) Date of Patent: Sep. 16, 2014

(54) METHOD AND COMPOSITIONS FOR IMPROVING PULMONARY HYPERTENSION

(75) Inventors: George Verlaan, Wageningen (NL); John A. St. Cyr, Coon Rapids, MN (US)

(73) Assignee: Bioenergy, Inc., Ham Lake, MN (US)

(*) Notice: Subject to any disclaimer, the term of this patent is extended or adjusted under 35 U.S.C. 154(b) by 1833 days.

(21) Appl. No.: 11/640,082

(22) Filed: Dec. 15, 2006

(65) Prior Publication Data

US 2008/0146514 A1   Jun. 19, 2008

(51) Int. Cl.
| | | |
|---|---|---|
| *A61K 31/7004* | (2006.01) | |
| *A61K 31/70* | (2006.01) | |
| *C07H 3/02* | (2006.01) | |
| *A61K 31/519* | (2006.01) | |

(52) U.S. Cl.
CPC ............ *A61K 31/519* (2013.01); *A61K 31/7004* (2013.01)
USPC ........................................... 514/23; 536/1.11

(58) Field of Classification Search
CPC . A61K 31/7004; A61K 31/70; A61K 31/519; A61K 2300/00
USPC ........................................ 514/23; 536/1.11
See application file for complete search history.

(56) References Cited

U.S. PATENT DOCUMENTS

| 6,218,366 | B1 | 4/2001 | St. Cyr et al. | |
|---|---|---|---|---|
| 6,420,342 | B1 * | 7/2002 | Hageman et al. ............... | 514/23 |
| 7,553,817 | B2 | 6/2009 | Butler et al. | |
| 2002/0022052 | A1 * | 2/2002 | Dransfield .................... | 424/449 |
| 2002/0119933 | A1 | 8/2002 | Butler et al. | |
| 2004/0087515 | A1 | 5/2004 | Butler et al. | |
| 2006/0269535 | A1 | 11/2006 | Naidu et al. | |

FOREIGN PATENT DOCUMENTS

| EP | 1 800 675 A1 | 6/2007 |
|---|---|---|
| WO | WO 01/85178 A1 | 11/2001 |
| WO | WO 02/09727 A1 | 2/2002 |
| WO | WO 04000042 A2 * | 12/2003 |
| WO | WO 2006/050585 A2 | 5/2006 |
| WO | WO 2006/050585 A3 | 5/2006 |
| WO | WO 2008/076295 A1 | 6/2008 |

OTHER PUBLICATIONS

Dweik, RA, "Pulmonary Hypertension," Cleveland Clinic Center for Continuing Education, Retrieved from the Internet:<URL:http://www.clevelandclinicmeded.com/medicalpubs/diseasemanagem... html>; Jun. 30, 2010, 11 pgs.
International Search Report for PCT/US2007/025477; 3 pgs.
International Preliminary Report on Patentability and Written Opinion for PCT/US2007/025477; 7 pgs.
Vidt, DG, "Hypertension," Cleveland Clinic Center for Continuing Education, Retrieved from the Internet:<URL:http://www.clevelandclinicmeded.com/medicalpubs/diseasemanagem... html>; Jun. 30, 2010, 9 pgs.
"Conjugated linoleic acid," from Wikipedia, the free encyclopedia, retrieved from the internet at <URL:http://en.wikipedia.org/wiki/Conjugated_linoleic_acid> on Feb. 17, 2011; 9 pgs.; last modified Feb. 12, 2011.
Dorland's Illustrated Medical Dictionary, $27_{th}$ Edition; cover page, title page and p. 799 (1988).
"*gamma*-Linolenic acid," from Wikipedia, the free encyclopedia, retrieved from the internet at <URL:http://en.wikipedia.org/wiki/Gamma-Linolenic_acid> on Feb. 17, 2011; 4 pgs.; last modified Feb. 3, 2011.
Stedman's Medical Dictionary, $27^{th}$ Edition; cover page, title page and pp. 855-856 (2000).

\* cited by examiner

*Primary Examiner* — Shaojia Anna Jiang
*Assistant Examiner* — Michael C Henry
(74) *Attorney, Agent, or Firm* — Mueting, Raasch & Gebhardt, P.A.

(57) ABSTRACT

This invention discloses a method and compositions for treatment or prevention of pulmonary hypertension in a mammal. Representative mammals include humans and horses. The invention further relates to supplements especially beneficial in preventing or stopping the progression of pulmonary hypertension. The supplements include ribose and folate. Additional nutrients include omega-3 fatty acids and gamma-linolenic acid.

24 Claims, 2 Drawing Sheets

METHOD AND COMPOSITIONS FOR IMPROVING PULMONARY HYPERTENSION

FIELD OF THE INVENTION

This invention pertains to a method for treatment or prevention of pulmonary hypertension in a patient. The invention further relates to supplements especially beneficial in stopping the progression of or reversing pulmonary hypertension.

BACKGROUND

Pulmonary hypertension (PHT) is a condition that is characterized by thickened arterial walls of the vessels in the lung. The condition may be congenital, primary PHT where the initial lesion is in the lungs or acquired PHT from failure of other members of the cardiac-pulmonary axis. Congenital PHT is generally due to a left-right shunt associated with ventricular or atrial septal defects or patent ductus arteriosus. Primary PHT may be caused by emphysema, chronic asthma, chronic obstructive pulmonary disease, pulmonary fibrosis, pulmonary embolism with parenchymal infarct and reactive pulmonary blood vessels or tissues. Some of the triggers for acquired PHT are exposure to toxins, infections, air pollutants, tobacco smoke, and residence at high altitudes. Whatever the nature, congenital, primary or acquired, PHT eventually leads to right ventricular hypertrophy with or without heart failure. Patients are able to compensate with conventional medical therapies and can stabilize for an indefinite time. Other patients afflicted with this condition die due to progressive heart decompensation or may require a heart/lung transplant.

While the underlying etiology of acquired PHT may not yet be known, one common factor leading to the condition may be that the pulmonary blood vessels and lung tissue are very sensitive to certain factors that trigger the development of the disease. Among these suspected factors are a preexisting condition of Raynaud's syndrome, appetite suppressants, cocaine, and congestive heart failure. Certain disease states such as emphysema, reactive airway disease, chronic obstructive pulmonary disease, HIV infection, scleroderma and systemic lupus erythematosus are often accompanied by PHT.

Treatment commonly is merely symptomatic. Methods of lowering of the vasculature's blood pressure in those patients with hypertension may give some relief.

U.S. Pat. No. 6,218,366 discloses a therapeutic method comprising administering ribose to a mammal in an effective amount to increase the tolerance of the mammal to hypoxia, wherein the hypoxia is due to cardiovascular disease, myocardial stunning, anaesthesia, surgical procedures, peripheral vascular disease, intermittent claudication, pulmonary dysfunction, physical exertion, pharmaceutical treatment, tachycardia or poisoning.

U.S. Pat. No. 6,420,342 discloses a nutritional composition, comprising ribose and folate in amounts which are effective to support total nucleotide metabolism, and 0.1 to eight grams of orotate per five grams of ribose.

WO/2006/050585 discloses a food product comprising at least one betine and L-arginine in a combined amount effective to induce and/or sustain a physiological increase in nitric oxide production in a mammal after ingesting said food product. This is claimed to be beneficial for the treatment of pulmonary hypertension by lowering the blood pressure.

The disadvantage of the known treatments is that there does not exist an optimal nutritional treatment that is focused on the problems related to pulmonary hypertension. Thus need remains for a nutritional therapy to limit the progression of pulmonary hypertension, whether congenital, primary or acquired.

SUMMARY OF THE INVENTION

The method of the invention comprises the administration of effective amounts of ribose and folate, either in combination or separately to a mammal suffering from pulmonary hypertension, whether congenital or acquired. Humans and horses are two examples of mammals presenting with pulmonary hypertension. According to the invention this is equivalent to the use of an effective amount of ribose and folate for treating a mammal suffering from pulmonary hypertension.

The inventors surprisingly found, when using a pulmonary hypertension model, that the oral supplementation of compositions comprising the combination of ribose and folate significantly improved the hemodynamic findings of pulmonary hypertension.

The effective amount of ribose is 0.5 to 40 grams D-ribose per day and the effective amount of folate is 100 micrograms to 20 milligrams folate per day. A preferred effective amount of D-ribose is one to 20 grams per day and a more preferred effective amount of folate is 250 micrograms to 15 milligrams per day. The most beneficial regimen is the daily dose administered in two or three portions. A most preferred effective amount of D-ribose is one to 15 grams per day and a most preferred effective amount of folate is 500 micrograms to five milligrams per day. A tolerable single dosage of ribose is 0.5 to 10 grams, most preferably 3-8 grams of ribose.

A further improvement of the invention is obtained when additional eicosopentanoic acid (EPA), and/or docosohexanoic acid (DHA) and gamma-linolenic acid (GLA) is used in the manufacture of a nutritional composition for use in a method for treating or prevention of decreased lung function and pulmonary hypertension.

Other mammals may experience chronic or episodic PHT. Race horses often have "hemorrhagic lung" due to extreme exertion, which leads to PHT and often right ventricular hypertrophy. When the mammal experiencing pulmonary hypertension is a horse, suitable adjustments must be made in the effective dosage. The preferred effective amount of ribose for a horse is 3 to 250 grams of ribose per day and the preferred effective amount of folate is 3 milligrams to 30 milligrams per day. A tolerable single dosage for horses is 30 to 80 grams of ribose.

DETAILED DESCRIPTION OF THE INVENTION

Definitions

Figure 1:
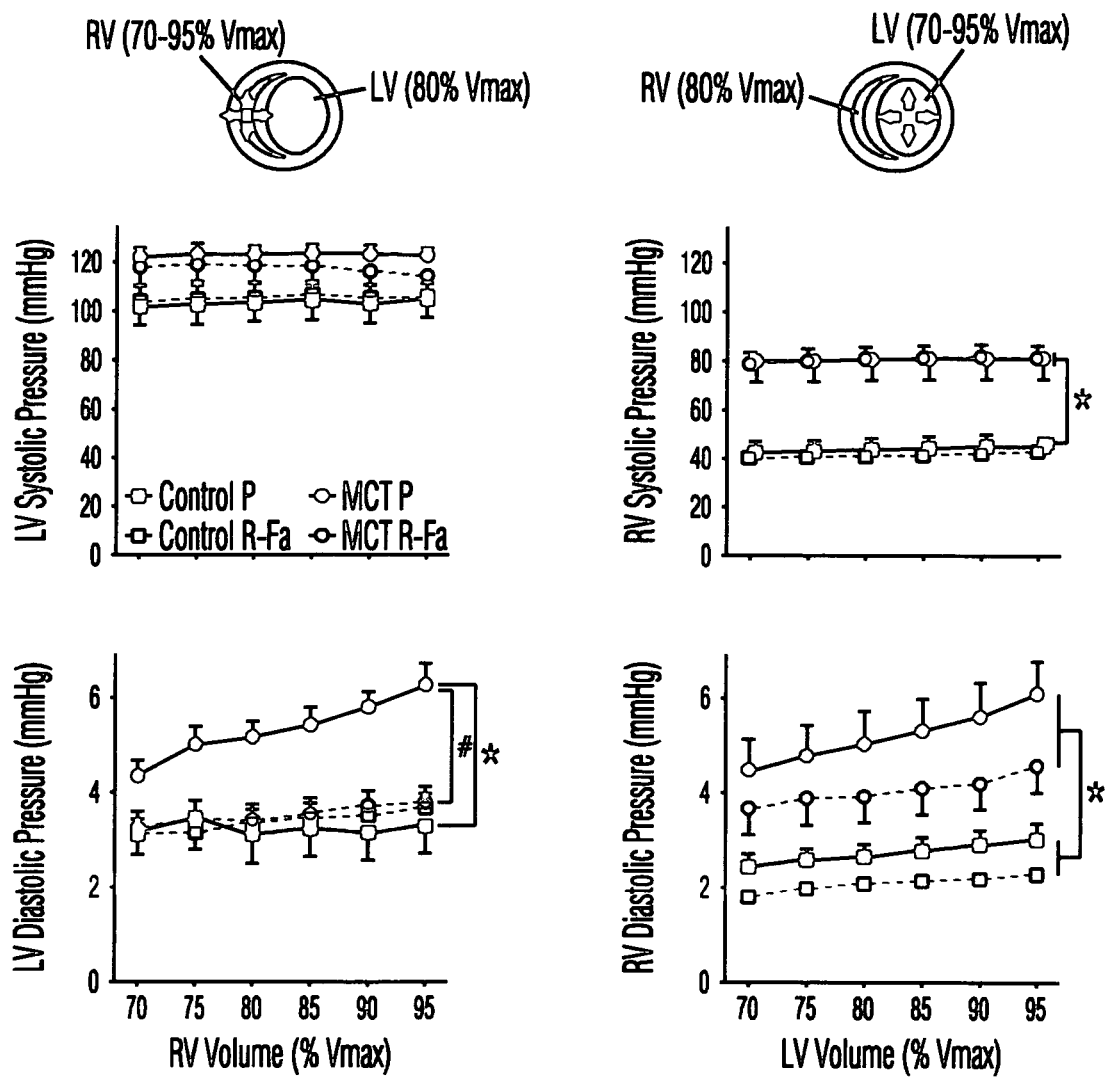
FIG. 1 shows hemodynamic measurements of MCT treated and control rats.

For purposes of this invention, the following terms have the following meaning:

Ribose: the term ribose is intended to include D-Ribose and other related compounds that are readily converted to ribose in vivo or which spare endogenous ribose. These compounds include ribitol, ribulose, 5-phosphoribose, xylitol, xylulose and sedoheptulose. Essentially pure, crystalline D-ribose is preferred. However, partially pure ribose isolated from yeast or produced by a bacterial fermentation may also be used, provided that the effective amount of D-ribose is contained in the crude product.

Ribose may be easily and inexpensively synthesized, or may be isolated from yeast or other natural sources, but is most conveniently produced by bacterial fermentation. The substrate can be any carbohydrate source, but is conveniently corn syrup. Likewise, the fermentation syrup or partially purified product may be used, provided that the amount of D-ribose is ascertained to be within the effective amounts described in this application. While essentially pure ribose is most desirable for formulations meant for human consumption, it is especially affordable to use a partially purified ribose for other mammals.

Folate: the term folate is intended to mean folic acid, folate esters and salts of folic acids, precursors and substitutes thereof. Substitutes include other one-carbon donors for biosynthesis, including, without limit, biotin. Biotin is known as a cofactor in carbon dioxide transfer to carboxylase enzymes and thus functions as a one-carbon donor.

Folic acid (Vitamin B9) is a multifunctional vitamin that is a one-carbon donor essential for many cellular syntheses, most importantly in the synthesis of the heme moiety, essential for the maturation of erythrocytes. A derivative of folic acid, 10-formyl-H4 PteGlu, is an essential co-factor in the formation of ATP via de novo purine synthesis. Since the function of folate is as a one-carbon donor for biosynthesis, it may be conjectured that other one-carbon donors may substitute for folate in the methods of this invention. One such substitute may be biotin.

Pulmonary hypertension (PHT) is defined as a condition in which the mean pressure in the pulmonary artery is at or above 20 mm of mercury. Normal mean pulmonary arterial pressure is approximately 14 mm of mercury. Early in the course of the condition, there may be no apparent symptoms. When they do occur, symptoms of pulmonary hypertension include shortness of breath even with minimal exertion, fatigue, chest pain, dizzy spells and fainting. Frequent causes of PHT include bronchitis, asthma, scleroderma or systemic lupus erythematosus (SLE). Other mammals may experience chronic or episodic PHT. Race horses often have "hemorrhagic lung" due to extreme exertion, which leads to PHT and often right ventricular hypertrophy. A prominent example is the famous race horse Secretariat. On necropsy, Secretariat had the largest heart ever seen in a thoroughbred horse, being at least three fold normal weight, presumably a sequela of the extreme exertion of his racing days.

Surprisingly, it was found that folate and ribose have a positive effect on pulmonary hypertension in an animal PHT model. Monocrotalin (MCT) induced PHT, which resulted, after 28 days, in marked right ventricular hypertrophy. In this model an improvement in measured heart function parameters can reflect a measure of improved pulmonary function, since the MCT-induced pulmonary malfunction causes the devastating effects on the heart function.

Accordingly, an embodiment according to this invention is a nutritional composition comprising ribose and folate for use in the manufacture of a nutritional composition for use in a method of treating or prevention of pulmonary hypertension in a patient, said method comprising the administration to a patient with pulmonary hypertension a nutritional composition comprising effective amounts of D-ribose and folate. This nutritional composition may benefit those exposed to risk factors for PHT, who have not yet shown symptoms of PHT. These risk factors include, but are not limited to, exposure to toxins, infections, air pollution, tobacco smoke, and residence at high altitudes.

When both ribose and folate are to be administered, the supplements are preferably combined in one formulation. Additional benefit is obtained when the mammal if co-administered a vasodilator, which may further enhance the distribution of the supplement within the body. The vasodilator may be given separately, but in an alternative embodiment, an effective amount of a vasodilator is added to the supplement formulation. The vasodilator may be L-arginine, nitroglycerine, nitrates, nitrites, papaverine, isoproterenol, nylidrin, isoxsurine, nitroprusside, adenosine xanthine, ethyl alcohol, dipyramide, hydrazaline, minoxidil, diazoxide or analogs of the foregoing. A most preferred vasodilator is L-arginine, preferably about six grams a day in one to four separate dosages may be used. When the vasodilator is nitroglycerine, a nitrate or a nitrite, ribose and folate are preferably administered orally about 15 minutes after the vasodilator is given buccally, sublingually or transdermally. This composition is administered from one to four times daily.

Another embodiment according to the invention may further comprise Coenzyme Q10 (CoQ10), which has been shown to result in a significant decrease in blood pressure in people with hypertension. Preferably at least 50 mg of CoQ10 per day is used, more preferably 100-500 mg CoQ10 is used per day.

In another preferred embodiment, the composition may further comprise eicosopentanoic acid (EPA) and/or docosohexanoic acid (DHA), the omega-3 fatty acids found in fish oil that has been shown to further lower blood pressure. Preferably, at least one gram per day of EPA and/or DHA and more preferably at least two grams per day are used since trials using two grams per day of omega-3 (as typically found in ten grams of fish oil) reported significant reductions in blood pressure, beneficial for patients with PHT. Preferably, EPA and/or DHA are present in combination with gamma-linolenic acid (GLA). This combination is preferred because GLA can partly replace EPA and DHA with similar efficiency on blood pressure, thereby improving the taste of the fish oil composition. The oil derived from vegetal seeds is also a good source of omega-3 oils and is a particularly good source for GLA. Included among these sources are flax, borage, soy beans and olive.

A preferred embodiment is a composition ribose and folic acid in a nutritionally complete formulation. Since patients with PHT often are undernourished, a nutritionally balanced food composition could be highly beneficial for the patient and could comprise the following: D-ribose between one and 25 grams per 100 grams dry weight of the composition and folate between 50 and 2000 micrograms per 100 grams dry weight of the composition and an amino acid source that provides at least 8% of the total caloric value of said food composition; and a fat that provides between 20 and 50% of the total caloric value of said food composition; and a carbohydrate or combination of different carbohydrates that provide the balance of the total caloric value of said food composition, wherein the fat comprises the omega-3 fatty acids EPA and/or DHA and preferably further comprising GLA in an amount between 15 and 45 weight percent of the total fatty acid content of the composition.

EXAMPLE 1

PHT Model

Monocrotalin (MCT), a phytotoxin pyrolizidine alkaloid, is a pneumotic agent, which causes hypertrophy of the pulmonary arterial bed. Upon administration, the molecule is activated in the liver and transported to the lungs. Adult Wistar rats weighing about 175 grams were injected subcutaneously with either 30 mg/kg body weight or 80 mg/kg body weight monocrotalin. Normal saline was injected as a control. Food and water were given ad libitum. A cross-section of pulmonary artery from a saline-injected, normal rat (left) and a cross-section of aorta from a rat treated with 30 mg MCT shows that the arterial wall in the treated rat is thicker in diameter than that of the untreated rat. This is representative of the primary lesion of PHT.

EXAMPLE 2

Treatment with Ribose and Folate

Adult Wistar rats (N-40) were randomized into four groups of ten as shown in Table I

TABLE I

| RAT | Placebo Control | MCT Control | Placebo Test | MCT Test |
|---|---|---|---|---|
| MCT | 0 | 30 mg/kg | 0 | 30 mg/kg |
| Dextrose | 150 mg/kg/day | 150 mg/kg/day | 0 | 0 |
| Ribose | 0 | 0 | 150 mg/kg/day | 150 mg/kg/day |
| Folate | 0 | 0 | 40 mg/kg/day | 40 mg/kg/day |

The supplements, dextrose and ribose/folate were fed in two ml of vanilla yogurt. After six weeks of supplementation, each rodent was sacrificed and myocardial function assessed using a Langendorff preparation. In the Langendorff preparation, the aorta is cannulated and the heart perfused with oxygenated perfusate in a retrograde fashion. Perfusate enters the coronary artery to maintain the heart with oxygen and nutrients. Any aerated normal saline with glucose added may be used. Both left and right ventricular intrachamber balloons provided ex vivo hemodynamic assessment.

FIG. 1 shows the effect on RV and LV volume changes from 70 to 95% Vmax on the averaged peak systolic and end-diastolic pressures from the LV (left panels) and RV (right panels) at 80% Vmax, respectively in control placebo (n=9), control R-Fa (n=10); MCT placebo (n=9) and MCT R-Fa (n=)10 hearts. An increase in RV volume resulted in an increase in LV diastolic pressure in the MCT placebo group, however, not in the control placebo group. Supplementary ribose/folate normalized the MCT-induced increase of LV diastolic pressures by RV volume increase. An increase in LV volume resulted in an increase in RV diastolic pressure, which was similar for all groups, and not influenced by ribose/folate supplementation. Values are expressed as mean±SEM*$p<0.05$ control vs. MCT, #$p<0.05$ placebo vs. ribose/folate in a two way ANOVA.

It is therefore concluded that the combination of ribose and folate significantly improves the hemodynamic findings in pulmonary hypertension compared to animals not fed ribose and folate.

Figure 2:
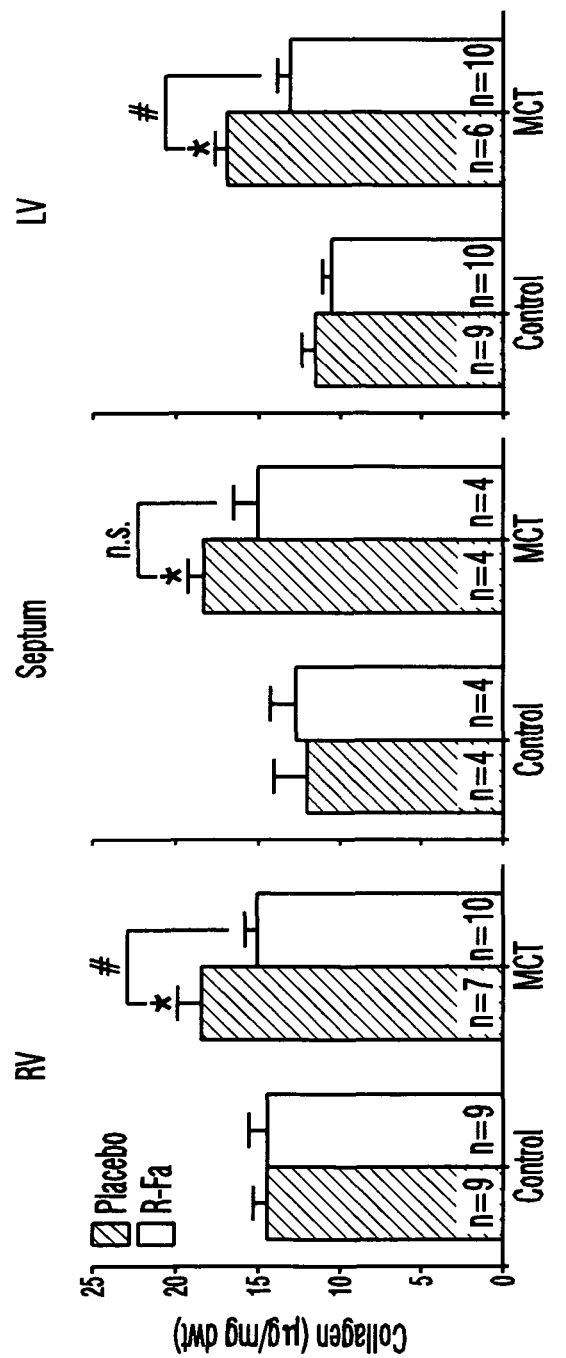
FIG. 2 shows collagen content in hearts of MCT treated and control rats.

FIG. 2 shows increased collagen content in the RV, septum and LV in hearts from the MCT Placebo groups. Supplementation with ribose and folate normalized the MCT-induced increase in collagen content in the RV and LV. Ribose and folate supplementation did not affect the collagen content in the control group. Values are expressed as means±SEM, *$p<0.05$ to control; #$p<0.05$ placebo vs. R-F; n.s—not significant.

EXAMPLE 3

Powder Nutritional Compositions Suitable for Treatment of Pulmonary Hypertension

| Ingredient | g/100 g powder |
|---|---|
| Ribose | 13 |
| Folic acid | 7.5 |
| Concentrated fish oil | 7.5 |
| Borage oil | 4 |
| Fructose | 12 |
| Caseinate | 13 |
| Lecithin powder | 0.16 |
| Vitamin B2 | 0.0012 |
| Ascorbyl palmitate | 0.016 |
| Carotenoid mix | 1.3 |
| Trace element mix | 0.09 |
| Vitamin premix | 0.228 |

EXAMPLE 4

Nutritional Compositions According to the Claimed Invention

| Protein | 20% of the total caloric value |
|---|---|
| Casein | 11 g |
| Whey protein | 11 |
| Carbohydrates | 60% of the total caloric value |
| Ribose | 5 g |
| Lactose | 6 |
| Maltose | 3 |
| Saccharose | 5 |
| GOS syrup | 7 |
| Polysaccharide | 40 |
| Fat | 20% of the total caloric value |
| Saturated fat | 1.8 g |
| Mono unsaturated | 5.8 |
| Poly unsaturated | 4.5 |
| EPA/DHA | 1.8 |
| Fiber | |
| Inulin | 0.5 g |
| Pectin hydrolysate | 5 |
| Vitamins and minerals | |
| Nutritional mix | 0.5 g |
| Folic Acid | 150 µg |

The preceding examples are representative of the invention and do not limit the scope thereof. Those skilled in the art may readily make substitutions and insubstantial variations without departing from the scope of the appended claims.

We claim:

1. A method of treating a patient with pulmonary hypertension comprising the administration of a composition comprising effective amounts of ribose and folate to the patient, wherein the composition further comprises gamma-linolenic acid (GLA).

2. The method of claim 1 wherein the composition further comprises eicosopentanoic acid (EPA) and/or docosohexanoic acid (DHA).

3. The method of claim 1 wherein the composition comprises:

ribose between one and 25 grams per 100 grams dry weight of the composition;

folate between 50 and 2000 micrograms per 100 grams dry weight of the composition;

an amino acid source that provides at least 8% of the total caloric value of the composition;

a fat that provides between 20 and 50% of the total caloric value of the composition; and a carbohydrate or combination of carbohydrates that provide the balance of the total caloric value of the composition.

4. The method of claim 1 wherein the composition further comprises L-arginine.

5. The method of claim 1 with the proviso that the patient does not exhibit hypertension.

6. The method of claim 1 wherein the patient is a mammal.

7. The method of claim 6 wherein the mammal is a human.

8. The method of claim 6 wherein the mammal is a horse.

9. The method of claim 1 wherein the effective amount of ribose is 0.5 to 40 grams of ribose per day and the effective amount of folate is 100 micrograms to 20 milligrams of folate per day.

10. The method of claim 9 wherein the effective amount of ribose is one to 20 grams per day and the effective amount of folate is 250 micrograms to 15 micrograms per day.

11. The method of claim 10 wherein the effective amount of ribose is one to 15 grams per day and the effective amount of folate is 500 micrograms to five milligrams per day.

12. The method of claim 1 wherein the patient is co-administered a vasodilator.

13. The method of claim 12 wherein the vasodilator is L-arginine, nitroglycerine, nitrates, nitrites, papaverine, isoproterenol, nylidrin, isoxsuprine, nitroprusside, adenosine, xanthine, ethyl alcohol, dipyramide, hydrazaline, minoxidil, or diazoxide.

14. A method of treating a patient with pulmonary hypertension comprising the administration of a composition comprising effective amounts of ribose and folate to the patient, wherein the composition comprises:

ribose between one and 25 grams per 100 grams dry weight of the composition;

folate between 50 and 2000 micrograms per 100 grams dry weight of the composition;

an amino acid source that provides at least 8% of the total caloric value of the composition;

a fat that provides between 20 and 50% of the total caloric value of the composition; and a carbohydrate or combination of carbohydrates that provide the balance of the total caloric value of the composition; and wherein the fat comprises (i) gamma-linolenic acid and (ii) eicosopentanoic acid (EPA) and/or docosohexanoic acid (DHA), wherein the total of (i) and (ii) are present in an amount between 15 and 45 weight percent of the total fat content of the composition.

15. The method of claim 14 wherein the composition further comprises eicosopentanoic acid (EPA) and/or docosohexanoic acid (DHA).

16. The method of claim 14 with the proviso that the patient does not exhibit hypertension.

17. The method of claim 14 wherein the patient is a mammal.

18. The method of claim 17 wherein the mammal is a human.

19. The method of claim 17 wherein the mammal is a horse.

20. The method of claim 14 wherein the effective amount of ribose is 0.5 to 40 grams of ribose per day and the effective amount of folate is 100 micrograms to 20 milligrams of folate per day.

21. The method of claim 20 wherein the effective amount of ribose is one to 20 grams per day and the effective amount of folate is 250 micrograms to 15 micrograms per day.

22. The method of claim 21 wherein the effective amount of ribose is one to 15 grams per day and the effective amount of folate is 500 micrograms to five milligrams per day.

23. The method of claim 14 wherein the patient is co-administered a vasodilator.

24. The method of claim 23 wherein the vasodilator is L-arginine, nitroglycerine, nitrates, nitrites, papaverine, isoproterenol, nylidrin, isoxsuprine, nitroprusside, adenosine, xanthine, ethyl alcohol, dipyramide, hydrazaline, minoxidil, or diazoxide.

* * * * *